United States Patent [19]

Hillyer

[11] Patent Number: 4,959,055
[45] Date of Patent: Sep. 25, 1990

[54] RETAINER FOR A PERCUTANEOUS TUBE

[76] Inventor: Janice L. Hillyer, 2880 Emerald St., Eugene, Oreg. 97403

[21] Appl. No.: 322,283

[22] Filed: Mar. 13, 1989

[51] Int. Cl.$^5$ ............................................. A61M 25/02
[52] U.S. Cl. ................................... 604/179; 604/278; 604/180
[58] Field of Search ............... 604/179, 178, 180, 278; 128/DIG. 26

[56] References Cited

U.S. PATENT DOCUMENTS

| | | | |
|---|---|---|---|
| 3,663,965 | 5/1972 | Lee, Jr. et al. | 3/1 |
| 3,893,446 | 7/1975 | Miller | 604/180 |
| 3,916,897 | 11/1975 | Elmore et al. | 604/179 |
| 4,265,244 | 5/1981 | Hill. | |
| 4,315,513 | 2/1982 | Nawash et al. | |
| 4,338,937 | 7/1982 | Lerman. | |
| 4,717,385 | 1/1988 | Cameron et al. | 128/DIG. 26 |

OTHER PUBLICATIONS

Feeding Gastrostomy—From the Journal of Enterostomal Therapy, Sep.-Oct. 1987 Edition.
The Gastrostomy Feeding Button—From Pediatric Nursing Jul.-Aug. Edition.

*Primary Examiner*—Stephen C. Pellegrino
*Attorney, Agent, or Firm*—James D. Givnan, Jr.

[57] ABSTRACT

A retainer of pliable construction having a conical portion for insertion into a fistula or other body opening to provide a seal to prevent outward passage of fluids. An end segment of the retainer is cylindrical and has an annular edge which grips the tube outer wall surface to prevent tube slippage. An open internal area of the retainer permits lateral tube displacement. A modified retainer receives multiple tubes. The retainer is held in place by an adhesive equipped strip rotatably positionable for securement to the body. The strip may be apertured at its ends for reception of a belt.

5 Claims, 1 Drawing Sheet

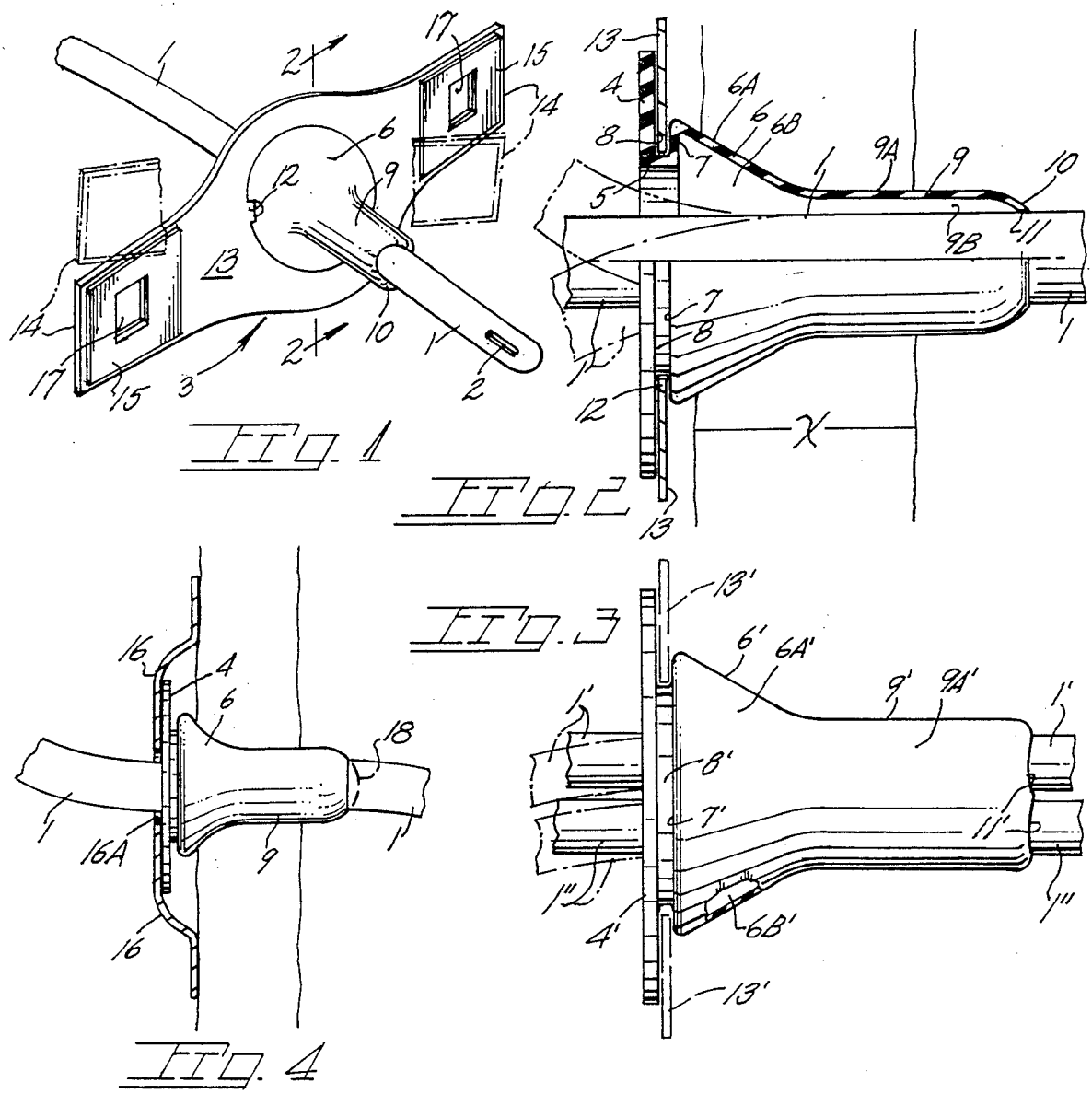

RETAINER FOR A PERCUTANEOUS TUBE

BACKGROUND OF THE INVENTION

The present invention pertains generally to securing a tube in place at the site of a body opening.

Gastrostomies utilize a tube inserted through a surgically created gastric fistula. The positioning of a tube through the abdominal and gastric walls encounters the risk of tube slippage and dislodgment. A variation consists of the tube terminating at a rigid device fixedly in place within the body opening. Such devices, termed buttons, overcome some of these problem areas, but require periodic care.

Another proposed solution to the problem is the disk shaped device in U. S. Pat. No. 3,663,965 which is embedded into the abdominal wall. A main body of the device is of solid construction having a central passageway receiving a tube which is secured to the device by an adhesive. The device is in the nature of an implant.

A problem with percutaneous tubes is peritubular seepage of fluids such as gastric juices resulting in their coming into contact with the patient's skin. Tissue damage by such fluids is a common problem.

SUMMARY OF THE PRESENT INVENTION

The present invention is embodied in a pliable tube retainer for adherence to the human body and with a conical projection of the retainer disposed within a surgically formed fistula.

The conical projection serves to seat against the fistula wall to prevent the passage of gastric fluids which may otherwise come into contact with and injure the skin. The outer surface of the present retainer effects a non-injurious seal with the interior surface of a fistual, stoma or tract. An opening in the projection is defined by an annular edge which grips the gastrostomy tube to retain same against slippage while permitting lateral flexing of the tube. The present device includes a base which is adapted for attachment to the body as by taping of an adhesive patch or an elastic belt. An annular groove in the device facilitates installation of a tab equipped adhesive strip for contact with the skin or an opening for belt attachment.

Objectives include the provision of a retainer for securing one or more percutaneous tubes in place and precluding peritubular discharge to prevent skin damage.

BRIEF DESCRIPTION OF THE DRAWINGS

In the accompanying drawings:

FIG. 1 is a perspective view of the present retainer;

FIG. 2 is a vertical sectional view taken along line 2—2 of FIG. 1 shown on an enlarged scale;

FIG. 3 is a side elevational view of a modified form of the retainer; and

FIG. 4 is a side elevational view of the present retainer secured in place by a patch.

DETAILED DESCRIPTION OF THE PREFERRED EMBODIMENTS

With continuing attention to the drawing wherein applied reference numerals indicate parts similarly hereinafter identified, the reference numeral 1 is a tube of resilient construction and of the type commonly used in a gastrostomy.

Such tubes serve as a conduit with discharge being via an opening at 2 which, in the case of a gastrostomy, is disposed in the stomach.

A tube retainer and seal is indicated generally at 3 and includes a base 4 defining an opening 5. Integral with base 4 is a conical projection 6 having an internal area 6B. Said projection has a rear annular wall 7, which in conjunction with base 4, defines a circular groove 8. The retainer, in addition to conical projection 6, includes an end segment 9 of generally cylindrical shape having a distal end 10 which defines a tube receiving aperture 11 sized to frictionally engage and grip the outside circumference of tube 1 while an internal area at 9B receives tube 1. The tube retainer is molded from an elastomeric material and is highly pliable by reason of the elasticity of the retainer material and wall thickness. The outer surface 6A of conical projection 6, as well as the exterior surface 9A of end segment 9, both engage body tissue defining a fistula. When the fistula is defined by the abdominal and gastric walls, the combined thickness may be indicated at X with conical projection 6 in seated, lightly biased engagement with abdominal tissue. Such engagement effects a seal against passage of gastric or other fluids which tend to move along the tube exterior. Gastric juices are, as earlier noted, injurious to the skin, hence the importance of providing a fluid tight seal. The surface 9A additionally serves to inhibit fluid flow by being in snug contact with the fistula.

With attention again to annular groove 8 between base 4 and projection rear wall 7, the groove may receive the inner margin 12 of flexible attachment means shown as a strip 13. Strip 13 is of flexible construction such as a synthetic plastic which readily flexes to permit tabs 14 thereon to be brought into contact with the abdominal surface A. For adherence to said surface, the tabs 14 are provided with adhesive surfaces 15 such as that marketed under the Registered Trademark Stomahesive. An inner edge of margin 12 of strip 13 is of a diameter to be movably carried in annular groove 8 so as to permit rotational positioning of the strip, per the broken line position of FIG. 1, to permit the adhesive patches 15 to be rotated for application to different areas of the abdomen exterior to avoid skin irritation. Openings at 17 in the strip 13 may receive the ends of a belt providing alternative attachment to the body. In FIG. 4 a flexible adhesive patch at 16 confines the present retainer in place in the fistula. The patch overlies base 4 and is centrally apertured at 16A to receive tube 1.

The present retainer is preferably of a molded, highly resilient material such as silicone rubber and inert with regard to body tissue to avoid irritation. The interior area 6B of the conical projection 6 is unobstructed to permit a range of lateral tube displacement per the broken line tube positions without trauma of body tissue. Axial displacement of the tube or tubes is prevented by the frictional engagement of aperture edge 11 and the tube exterior without constriction of the tube.

The present retainer is usable in a fistula the interior of which has at least partially healed from the surgery forming same.

In the modified form of the retainer, all parts corresponding to those above described are identified by like prime reference numerals. Distal end 10' defines a pair of apertures 11' each receiving in a frictional engaging manner a tube 1' and 1". As in the first described form of the retainer, the tubes 1' and 1" may flex laterally in area 6B' to some extent without imparting discomfort to the patient.

The present retainer may be constructed from an elastomeric material as for example silicone rubber as currently used in the molding of nipples for feeding bottles for infants. As shown in FIG. 4 in phantom lines, the retainer may be formed with a closed end at 18 to serve as a closure for a fistula or other body opening.

While I have shown but a few embodiments of the invention, it will be apparent to those skilled in the art that the invention may be embodied still otherwise without departing from the spirit and scope of the invention.

Having thus described the invention, what is desired to be secured by a Letters Patent is:

1. A retainer for flexible tube entering an opening in the human body and comprising in combination,
   a base for disposition adjacent an opening in the body,
   flexible attachment means on said base and adapted for attachment to the exterior of the body,
   a conical projection on said base of a highly resilient nature including an end segment, said conical projection for partial insertion into the body opening so as to surfacially engage body tissue defining said opening to provide a seal therewith, said end segment having an annular edge for frictional engagement with the tube outer wall to retain same against axial displacement, said base and said conical projection defining a circular groove, said flexible attachment means having an inner edge rotatably confined in said groove.

2. The retainer claimed in claim 1 wherein said conical projection defines an unobstructed area within which the tube may move laterally.

3. The retainer claimed in claim 1 wherein said end segment includes multiple annular edges each for frictional engagement with a tube to retain same against axial displacement.

4. The retainer claimed in claim 1 wherein said flexible attachment means defines openings for passage of a belt.

5. The retainer claimed in claim 1 wherein upon removal of said conical projection from the flexible attachment means a substitute conical projection may be engaged with the flexible attachment means, said substitute conical projection having a closed end serving to provide a closure for the body opening.

* * * * *